US010299864B1

(12) United States Patent
Yu

(10) Patent No.: US 10,299,864 B1
(45) Date of Patent: May 28, 2019

(54) CO-LOCALIZATION OF MULTIPLE INTERNAL ORGANS BASED ON IMAGES OBTAINED DURING SURGERY

(71) Applicant: SONY CORPORATION, Tokyo (JP)

(72) Inventor: Liangyin Yu, San Jose, CA (US)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/056,755

(22) Filed: Aug. 7, 2018

(51) Int. Cl.
  *A61B 34/10* (2016.01)
  *G06T 7/11* (2017.01)
  *G06K 9/62* (2006.01)
  *A61B 1/04* (2006.01)
  *A61B 1/313* (2006.01)
  *A61B 34/20* (2016.01)
  (Continued)

(52) U.S. Cl.
  CPC .......... *A61B 34/10* (2016.02); *A61B 1/00016* (2013.01); *A61B 1/04* (2013.01); *A61B 1/3132* (2013.01); *A61B 34/20* (2016.02); *G06K 9/6256* (2013.01); *G06K 9/6277* (2013.01); *G06T 7/11* (2017.01); *G06T 7/70* (2017.01); *A61B 2034/107* (2016.02); *A61B 2034/2057* (2016.02); *A61B 2034/2065* (2016.02); *A61B 2090/373* (2016.02); *G06T 2207/10016* (2013.01); *G06T 2207/20076* (2013.01); *G06T 2207/20081* (2013.01); *G06T 2207/30204* (2013.01)

(58) Field of Classification Search
  CPC ....... A61B 34/20; A61B 1/00016; A61B 1/04; A61B 1/3132; G06T 7/11; G06T 7/70; G06K 9/6256; G06K 9/6277
  See application file for complete search history.

(56) References Cited

U.S. PATENT DOCUMENTS 8,792,963 B2   7/2014   Zhao et al.
9,547,940 B1   1/2017   Sun et al.
(Continued)

FOREIGN PATENT DOCUMENTS

WO   2016/195698 A1   12/2016

OTHER PUBLICATIONS

Tong, et al., "Medical Image Analysis", Medical ImageAnalysis 23, Elsevier, 2015, pp. 92-104.
(Continued)

*Primary Examiner* — Edward Park
(74) *Attorney, Agent, or Firm* — Chip Law Group

(57) ABSTRACT

A surgical assistive device, which handles co-localization of an internal organ of interest and a neighboring organ based on images obtained during surgery, selects a test video frame from a sequence of video frames and generates first localization likelihood values and second localization likelihood values for the internal organ of interest and the neighboring organ, respectively. The surgical assistive device determines extent of anatomical adjacency boundary between the internal organ of interest and the neighboring organ, based on the first localization likelihood values and the second localization likelihood values. The surgical assistive device segments the test video frame into a plurality of regions and generates a first region based on integration of a first set of regions from the plurality of regions. The surgical assistive device further localizes the internal organ of interest based on first region, in accordance with the extent of anatomical adjacency boundary.

21 Claims, 8 Drawing Sheets

(51) Int. Cl.
*A61B 1/00* (2006.01)
*G06T 7/70* (2017.01)
*A61B 90/00* (2016.01)

(56) References Cited

U.S. PATENT DOCUMENTS

2005/0105795 A1* 5/2005 Singh .................. G06K 9/6232
382/160
2018/0329225 A1* 11/2018 Kleckner ........... G01N 21/6458

OTHER PUBLICATIONS

Wolz, et al., "Automated Abdominal Multi-Organ Segmentation With Subject-Specific Atlas Generation", IEEE Transactions on Medical Imaging, vol. 32, No. 9, Sep. 2013, pp. 1723-1730.

* cited by examiner

CO-LOCALIZATION OF MULTIPLE INTERNAL ORGANS BASED ON IMAGES OBTAINED DURING SURGERY

CROSS-REFERENCE TO RELATED APPLICATIONS/INCORPORATION BY REFERENCE

None.

FIELD

Various embodiments of the disclosure relate to multiple organs co-localization and associated computer-assisted surgery technologies. More specifically, various embodiments of the disclosure relate to a surgical assistive device that handles co-localization of multiple internal organs based on images obtained during surgery.

BACKGROUND

Advancements in the field of medical imaging techniques and associated sensors and/or devices have facilitated use of display devices that help visualize interior of a human or an animal body during clinical analysis and surgical procedures. The visualization is usually done by a surgeon who physically inserts an instrument embedded with a miniaturized camera inside the body of a patient, via an incision or an opening in the body of the patient. For example, a surgeon may insert a laparoscope within the body of a patient to visualize different internal organs, such as liver, spleen, kidney, and the like, on a screen during surgery or a clinical examination. The foremost reason to visualize such internal organs is associated with an estimation of the locations of specific organ of interest within the body of the patient within a region associated with the incision in the body.

Different organs have different characteristics and the precision to find the different organs may also vary. In practice, the visibility of such specific internal organs on the display screen may be affected by, for example, presence of blood, gases, and/or tissues that may lie in a field-of-view (FOV) of the instrument. The view of the internal organ may be further blocked by tumor growths on the same internal organ or other neighboring organs and the presence of such abnormal cell growth may change the appearance of the internal organ. Additionally, certain patients' may exhibit variations in anatomical features of specific internal organs, such as variations in position, size, shape, and appearance of the internal organ, which may be caused by an infection, abnormality, or a disease. Further, performing surgery on a specific area of an internal organs may be complicated due to the presence of other closely connected organs in the body of the patient. A mere assumption of the location and a particular region of the internal organ from a given visual on the screen during surgery may lead to errors in a surgical procedure. The accuracy of such assumptions may further depend upon an experience level of the surgeon and therefore, improved systems may be required to provide an enhanced assistance during surgery.

Further limitations and disadvantages of conventional and traditional approaches will become apparent to one skilled in the art, through comparison of described systems with some aspects of the present disclosure, as set forth in the remainder of the present application and with reference to the drawings.

SUMMARY

A surgical assistive device and method are provided for co-localization of an internal organ of interest and a neighboring organ based on images obtained during surgery, as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Certain embodiments of the disclosure may be found in a surgical assistive device and method for co-localization of an internal organ of interest and a neighboring organ that has an anatomical adjacency with the internal organ of interest, based on images obtained during surgery. Various embodiments of the disclosure may provide a surgical assistive device. The surgical assistive device may include a surgical image capture device and a co-localization circuitry communicatively coupled to the surgical image capture device. The surgical image capture device (e.g., an imaging laparoscope) may be configured to capture a sequence of video frames. The internal organ of interest (e.g., stomach) and the at least one neighboring organ (e.g., liver) may be localized concurrently or sequentially in a test video frame of the captured sequence of video frames. The internal organ of interest may be localized post the localization of at least one neighboring organ. The localization of the internal organ of interest may be done based on prior knowledge (or estimation of) of localization of the neighboring organ and an anatomical adjacency boundary between the internal organ of interest and the neighboring organ. The surgical assistive device enables localization of the internal organ of interest and the neighboring organ with enhanced precision to assist a surgeon in image-guided surgery and to accurately track the internal organ of interest and the neighboring organ of a subject in real time or near-real time during surgery. The co-localization of the internal organ of interest and the neighboring organ localized by the surgical assistive device may further facilitate a navigation of the surgical instrument or tool within the body of the subject to reach to a localized region of the internal organ of interest with minimum damage to tissues, while reaching to the localized region.

Figure 1:
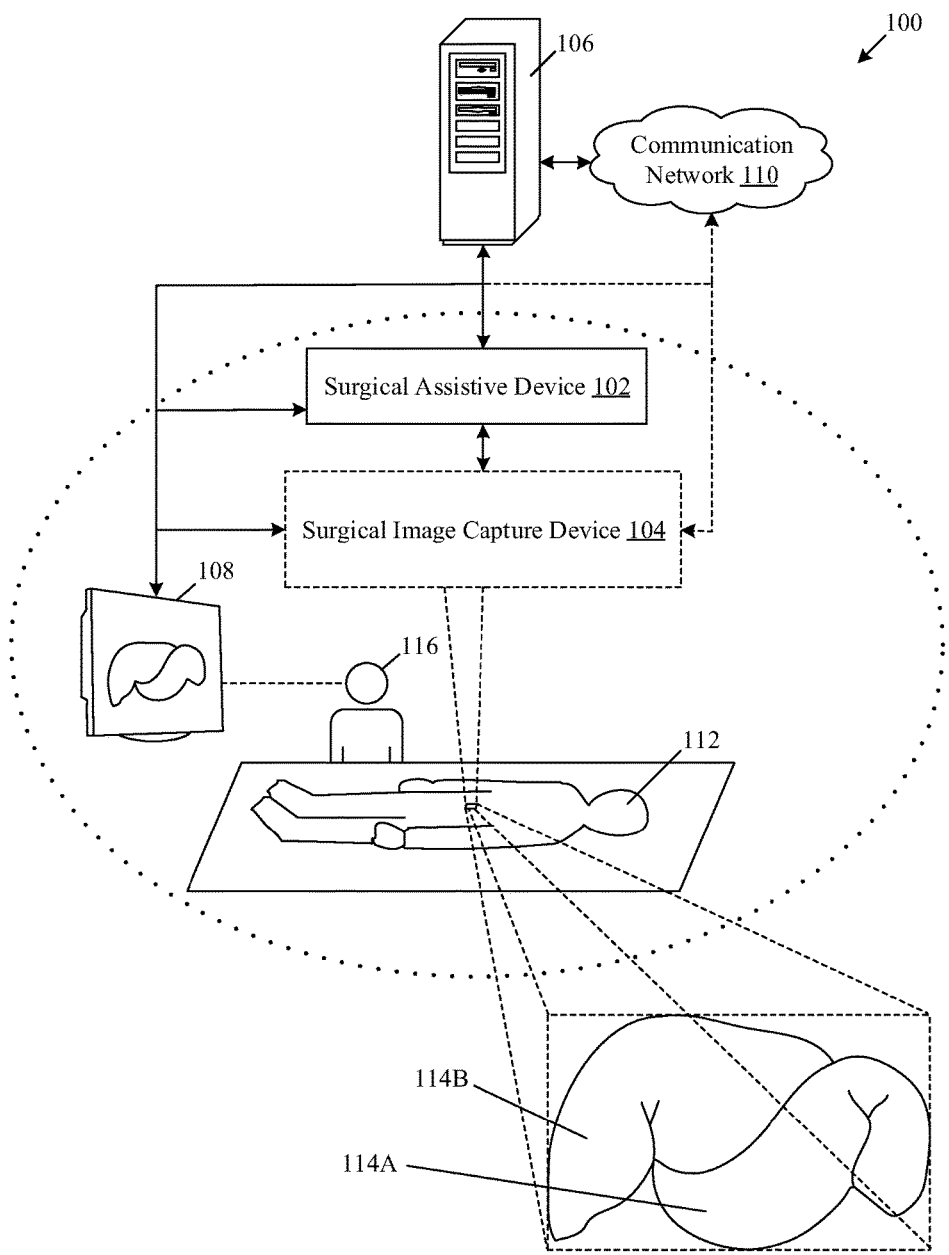
FIG. 1 is a diagram that illustrates a network environment that facilitates co-localization of an internal organ of interest and a neighboring organ based on images obtained during surgery of a subject, to provide assistance during surgery, in accordance with an embodiment of the disclosure.

FIG. 1 is a diagram that illustrates a network environment that facilitates co-localization of an internal organ of interest and a neighboring organ based on images obtained during surgery of a subject, to provide assistance during surgery, in accordance with an embodiment of the disclosure. With reference to FIG. 1, there is shown a network environment 100 that may include a surgical assistive device 102, a surgical image capture device 104, a medical data server 106, and a display device 108. In some embodiments, the surgical assistive device 102 may include the display device 108, instead of having an externally coupled device.

There is further shown a subject, such as a human subject 112, an internal organ of interest 114A and a neighboring organ 114B that has an anatomical adjacency with the internal organ of interest 114A of the human subject 112, and a surgeon 116. In quantitative terms, the anatomical adjacency may indicate relative coordinates and relative position of the internal organ of interest 114A in relation to the neighboring organ 114B in a sequence of video frames captured by the surgical image capture device 104. The surgical assistive device 102 may be communicatively coupled to the surgical image capture device 104, and the medical data server 106, via a communication network 110.

The surgical assistive device 102 may comprise suitable logic, circuitry, and interfaces that may be configured to localize the internal organ of interest 114A (e.g., stomach) and the neighboring organ 114B (e.g., liver), based on a mutual anatomical adjacency between the internal organ of interest 114A and the neighboring organ 114B. The surgical assistive device 102 may facilitate the surgeon 116 (or an observer) to precisely locate the internal organ of interest 114A within the body of the human subject 112 based on images captured during the surgery of the human subject 112. In some cases, the surgical assistive device 102 may render a real-time or near real-time assistance to the surgeon 116 by presenting supplemental information (e.g., posterior localization information) on intraoperative images (e.g., a test image that has a maximum likelihood of the internal organ of interest 114A and the neighboring organ 114B). The surgical assistive device 102 may be a computer-assisted surgical system, a robot-assisted surgical system, a medical imaging device (e.g., an open Magnetic Resonance Imaging (MRI) machine), an electronic surgical instrument (such as a laparoscope), a display device (e.g., the display device 108), and/or other medical-grade computing devices.

In accordance with an embodiment, the surgical assistive device 102 may further include a surgical image capture device 104. The surgical image capture device 104 may be configured to capture one or more video frames of the internal organ of interest 114A and the neighboring organ 114B of the human subject 112 when surgery or diagnostic procedure is performed on the internal organ of interest 114A and/or the neighboring organ 114B. Alternatively, the surgical assistive device 102 may be communicatively coupled to the surgical image capture device 104, via the communication network 110. Examples of the surgical image capture device 104 may include, but are not limited to, an endoscopic/laparoscopic camera, a medical resonance imaging (MRI) device, a computer tomography (CT) scanning device, a minimally invasive medical imaging device, and/or a minimal incision medical imaging device.

The medical data server 106 may comprise suitable logic, circuitry, and interfaces that may be configured to store training data related to an appearance of the internal organ of interest 114A and the neighboring organ 114B. In accordance with an embodiment, the medical data server 106 may be configured to provide pre-stored versions of the training data to the surgical assistive device 102, via the communication network 110. In accordance with an embodiment, the surgical assistive device 102 may directly receive the training data from an external database (not shown in the figure) that may be different from the medical data server 106.

In accordance with an embodiment, both the medical data server 106 and the surgical assistive device 102 may be integrated as a computer-assisted system. In some embodiments, the medical data server 106 may be implemented through a plurality of cloud-based resources by use of several technologies that are well known to those skilled in the art. In other embodiments, the functionalities of the medical data server 106 may be implemented by the surgical assistive device 102, without a departure from the scope of the disclosure. The medical data server 106 may be compliant with one or more standards or requirements such as Health Insurance Portability and Accountability Act (HIPAA)-compliant medical data server that may include at least one of a cloud storage, a virtual cloud storage, or an on premise data storage.

The display device 108 may comprise suitable logic, circuitry, and interfaces that may be configured to display supplemental information over localized region(s) of the internal organ of interest 114A and/or the neighboring organ 114B in a sequence of video frames. A user, such as the surgeon 116, of the display device 108 may control the surgical assistive device 102, with visual support, instructions, and/or guidance from a user-interface of the display device 108. In accordance with an embodiment, the display device 108 may be configured to display a test video frame from the sequence of video frames, in real time or near-real time, while the surgical or diagnostic procedure is performed on the internal organ of interest 114A of the human subject 112. The display device 108 may be further configured to display a localized region of the internal organ of interest 114A and the neighboring organ 114B of the human subject 112. The localized region of the internal organ of interest 114A and the neighboring organ 114B may be displayed with the help of supplemental information related to the internal organ of interest 114A and the neighboring organ 114B of the human subject 112.

The display device 108 may be a portable electronic device (e.g., a smartphone or a tablet), a wearable electronic device (e.g., a virtual reality/augmented reality/mixed reality (VR/AR/MR) headset), a non-portable electronic device (e.g., a personal desktop computer), and a medical device (e.g., open MRI) inside an operation theatre where the human subject 112 may undergo a surgery. Also, in some cases, the display device 108 may be a surgical display or a medical grade surgical display, a surgical Heads-up-display (HUD), a surgical High Definition (HD) (Microscopic Resolution) display, a surgical grade wearable AR information display, a 3D/2D surgical display, and a 3D Head Mounted Display.

In accordance with an embodiment, the display device 108 may be integrated with the surgical assistive device 102. Alternatively, the display device 108 may be communicatively coupled to the surgical assistive device 102. A user, such as the surgeon 116, of the display device 108 may control the surgical assistive device 102, with visual support, instructions, and/or guidance from a user-interface of the display device 108.

The communication network 110 may include a medium through which the surgical assistive device 102, the surgical image capture device 104, and/or the medical data server 106 may communicate with each other. The communication network 110 may be a wired or wireless communication network. Examples of the communication network 110 may include, but are not limited to, a Local Area Network (LAN), a Wireless Local Area Network (WLAN), a cloud network, a Long Term Evolution (LTE) network, a plain old telephone service (POTS), a Metropolitan Area Network (MAN), and/or the Internet. Various devices in the network environment 100 may be configured to connect to the communication network 110, in accordance with various wired and wireless communication protocols. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, cellular communication protocols, and/or Bluetooth (BT) communication protocols.

In operation, the surgical assistive device 102 may be utilized by a user (e.g., the surgeon 116) to perform a surgical or diagnostic procedure on the internal organ of interest 114A and the neighboring organ 114B of a subject, for example, the human subject 112. The surgical or diagnostic procedure may be a minimally invasive surgery/diagnosis, a minimal incision surgery/diagnosis, a laparoscopic procedure, an endoscopic procedure, and/or other surgical procedures. In accordance with the surgical procedure, the surgeon 116 may insert the surgical image capture device 104 in a specific region, such as an abdominal region, of the body of the human subject 112. The surgical image capture device 104 may be attached to an instrument, such as a laparoscope and may further include an image sensor (not shown) to capture a sequence of video frames within the body of the human subject 112. For example, the surgical image capture device 104 may be attached to one end of the laparoscope. The laparoscope that may carry the surgical image capture device 104 may be further inserted through an incision in the body of the human subject 112. For example, the surgeon 116 may want to localize the internal organ of interest 114A in the body of the human subject 112 for computer assisted navigation of a surgical tool or instrument within the body of the human subject 112. Such computer assisted navigation may further facilitate the surgeon 116 in image guided surgery to track the internal organ of interest 114A of the subject.

In certain embodiments, the internal organ of interest 114A may be an abdominal organ, for example, the stomach, which the surgeon 116 may want to precisely locate inside the body of the subject during a laparoscopic surgery. In other embodiments, the internal organ of interest 114A may be liver, pancreas, spleen, kidneys, lungs, and the like. For certain surgical procedures and/or medical examinations, the visibility of the internal organ of interest 114A may be affected due to a presence of different occluding elements, such as blood, gases, tissues, and tumors, in a field-of-view (FOV) of the surgical image capture device 104. In one case, the FOV of the internal organ of interest 114A may be blocked by a tumor growth on the same organ or neighboring organs. The presence of abnormal cell growth (that causes tumor growth) may change the appearance of the internal organ of interest 114A that is to be examined, resected, or subjected to a specific surgical procedure by the surgeon 116. In another case, the internal organ of interest 114A may be very small in size as compared to other abdominal organs in the body of the human subject 112. Further, when the human subject 112 is a child, the size of the internal organ of interest 114A may be relatively smaller than that of an adult, which further causes difficulty the localization of the internal organ of interest 114A.

Certain subjects may have different anatomical structures that may cause variations in the position, size, shape, and appearance of the internal organ associated with such anatomical structures, for example, an abdominal organ. In certain scenarios, the appearance of the organ of interest 114A of the human subject 112 may be different from the normal appearance due to an infection or a disease. Thus, a location of the internal organ of interest 114A may be imperfectly assumed within body of the human subject 112 as a result of the inherent anatomical structure variations and complexity of the internal organs during surgery. Such imprecise assumptions for the location of the internal organ of interest 114A may negatively impact an accuracy and a proficiency of the surgeon 116 while performing surgery and may further put safety of the human subject 112 at risk. Therefore, the surgical assistive device 102 may be configured to assist the surgeon 116 in a way that appearance complexities and location-based bias may be reduced, and a safe, accurate, and quick assistance may be provided during surgery.

The aforementioned issues may be addressed by robustly localizing the internal organ of interest 114A (e.g. the stomach) in different intraoperative images (e.g., images captured by the surgical image capture device 104 during surgery) based on known or pre-estimated likelihood of the neighboring organ 114B (e.g., the liver) and mutual anatomical adjacency between the internal organ of interest 114A and the neighboring organ 114B. The localization of the internal organ of interest 114A and the neighboring organ 114B may mitigate a bias of the surgeon 116 or a robotic surgical system generated based on abnormal appearance, growth, variations in anatomical structure, like size, and other factors.

In accordance with an embodiment, the surgical image capture device 104 may be configured to capture a sequence of video frames (e.g., a continuous video feed) of two or more internal organs of the human subject 112. The sequence of video frames may be captured based on insertion of the surgical image capture device 104 in the body of the human subject 112, via an incision or a specific passage within the body of the human subject 112. The captured sequence of video frames may include a portion or an entire view of the two or more internal organs of the human subject 112. Alternatively stated, the sequence of video frames may be captured with a maximum likelihood of presence of the internal organ of interest 114A and the neighboring organ 114B in at least one video frame of the sequence of video frames. The maximum likelihood of presence of the internal organ of interest 114A and the neighboring organ 114B may further increases a likelihood of an anatomical adjacency boundary in the sequence of video frames.

In accordance with an embodiment, the surgical assistive device 102 may be configured to receive the captured sequence of video frames from the surgical image capture device 104. As the captured sequence of video frames may include a portion or an entire view of different internal organs of the human subject 112, certain images may be selected from the captured sequence of video frames for further processing to avoid selection of unwanted image frames. For example, selected images may capture a view of internal organs from different viewing angles. The unwanted image frames may have a view where the internal organ of interest 114A and the neighboring organ 114B may be absent or a quality score of the view may be less than a threshold quality as a result of presence of other anatomical portions of the human subject 112. In accordance with an embodiment, the surgical assistive device 102 may be further configured to select a test video frame from the received sequence of video frames. The selection of the test video frame from the captured sequence of video frames may be based on a presence of at least two organs in a field-of-view of the surgical image capture device 104.

In accordance with an embodiment, the surgical assistive device 102 may be further configured to receive training data related to the appearance of the internal organ of interest 114A and the neighboring organ 114B from the medical data server 106. The received training data may further include a first set of training patches of the internal organ of interest 114A and a second set of training patches of the neighboring organ 114B. The first set of training patches for the internal organ of interest 114A and the second set of training patches for the neighboring organ 114B may be received from the training data by a random sampling technique. The random sampling technique may be executed based on the selected test video frame. In accordance with an embodiment, the random sampling technique may correspond to Monte Carlo sampling technique. Each training patch may include a sample portion (e.g., a training sample from an image obtained from different healthy test subject or unhealthy test subject) of a specific internal organ with a specific color, a texture, a number of veins, and other appearance parameters that uniquely defines the appearance of an internal organ (e.g., the internal organ of interest 114A and the neighboring organ 114B).

The surgical assistive device 102 may be configured to generate first localization likelihood values and second localization likelihood values for an internal organ of interest 114A and the neighboring organ 114B, respectively. The first localization likelihood values and the second localization likelihood values may indicate an appearance-based likelihood of presence of the internal organ of interest 114A and the neighboring organ 114B in a test video frame sampled from the captured sequence of video frames. The neighboring organ 114B may have an anatomical adjacency with the internal organ of interest 114A in the test video frame. Alternatively stated, for a known (or pre-estimated) likelihood of presence of the neighboring organ 114B, a likelihood of presence of a portion of the internal organ of interest 114A and/or an anatomical adjacency boundary between the internal organ of interest 114A and the neighboring organ 114B may be present in the test video frame.

The first localization likelihood values and the second localization likelihood values may be generated based on the test video frame and the received training data for the internal organ of interest 114A and the neighboring organ 114B. The first localization likelihood values may include conditional probability values that may indicate a likelihood of the internal organ of interest 114A in a set of test patches of the test video frame with respect to the extracted first set of training patches. Similarly, the second localization likelihood values may include conditional probability values that may indicate a likelihood of the internal organ of interest 114A in a set of test patches of the test video frame with respect to the extracted second set of training patches for the neighboring organ 114B.

In accordance with an embodiment, the first localization likelihood values may be generated by a comparison of each extracted training patch of the first set of training patches with each test patch in the set of test patches of the test video frame. In accordance with an embodiment, the second localization likelihood values may be generated by a comparison of each extracted training patch of the second set of training patches with each test patch in the set of test patches of the test video frame. In accordance with an embodiment, the first localization likelihood values for the internal organ of interest 114A and the second localization likelihood values for the neighboring organ 114B may be computed independent of each other.

The surgical assistive device 102 may be further configured to compute an anatomical adjacency boundary between the internal organ of interest 114A and the neighboring organ 114B, based on the generated first localization likelihood values and the generated second localization likelihood values. An extent (or a thickness) of an anatomical adjacency boundary may be further determined in the test video frame. The surgical assistive device 102 may determine the extent of anatomical adjacency boundary between the internal organ of interest 114A and the neighboring organ 114B. The determination of the extent of the anatomical adjacency boundary may be done further based on a degree of correlation between the generated first localization likelihood values and the generated second localization likelihood values for the internal organ of interest 114A and the neighboring organ 114B in the test video frame. The extent of the anatomical adjacency boundary may indicate a strength of a likelihood of presence (e.g., increased conditional probability values) of at least a portion of the internal organ of interest 114A and the neighboring organ 114B. The extent of the anatomical adjacency boundary may be represented by an area occupied by a region (as shown in FIG. 3B). The region may correspond to certain test patches (extracted from the test video frame), for which a correlation of the first localization likelihood values and the second localization likelihood values may lie above a threshold likelihood value. In certain embodiments, the correlation may be represented by a matrix product between a localization likelihood matrix for the internal organ of interest 114A and a corresponding localization likelihood matrix for the neighboring organ 114B.

In accordance with an embodiment, the computed anatomical adjacency boundary may be utilized for a precise classification (or identification) of the internal organ of interest 114A from the neighboring organ 114B when the extent of the computed anatomical adjacency boundary is maximum. The precise classification may be obtained based on a maximum degree of correlation between the generated first localization likelihood values and the generated second localization likelihood values. Alternatively stated, for precise classification and localization in test image, a stronger correlation of likelihood values for the internal organ of interest 114A and the neighboring organ 114B, respectively, may indicate presence of a stronger boundary between the neighboring organ 114B and the internal organ of interest 114A.

The surgical assistive device 102 may be further configured to segment the test video frame into a plurality of regions. Segmentation may cluster pixels that have similar characteristics into one region. Therefore, the test video frame may be segmented into a plurality of regions based on similar pixel values in the test video frame. The test video frame may be segmented using techniques that may be known to one ordinarily skilled in the art, and therefore, the details of the segmentation has been omitted from the disclosure for the sake of brevity.

The surgical assistive device 102 may be further configured to generate a first region for the internal organ of interest 114A based on an integration of a first set of regions from the plurality of regions in the segmented test video frame. The first set of regions may partially or completely correspond to a region occupied by the internal organ of interest 114A in the test video frame. The first set of regions may be integrated based on a conditional probabilistic distribution over each patch of the segmented test video frame. The probabilistic distribution may indicate a likelihood of a localization parameter for the internal organ of interest 114A in the segmented test video frame measured with respect to a likelihood of the anatomical adjacency boundary in the test video frame and a localization parameter for the neighboring organ 114B in the segmented test video frame. Also, in some embodiments, the first set of regions may be integrated based on edges of different segmented regions in the segmented test video frame.

The surgical assistive device 102 may be further configured to localize the internal organ of interest 114A based on the generated first region in the test video frame, in accordance with the extent of the anatomical adjacency boundary. The generated first region may exhibit a maximum posterior of probabilistic distribution for a localization parameter for the internal organ of interest 114A such that the internal organ of interest 114A and the neighboring organ 114B may be precisely distinguished in the test video frame.

In some embodiments, the surgical assistive device 102 may be configured to integrate a second set of regions from the plurality of regions in the segmented test video frame. The second set of regions may partially or completely correspond to a region occupied by the neighboring organ 114B in the test video frame. The second set of regions may be integrated based on the generated second localization likelihood values for the neighboring organ 114B. The surgical assistive device 102 may be further configured to generate a second region in the test video frame for the neighboring organ 114B based on integration of the second set of regions from the plurality of regions in the segmented test video frame.

The surgical assistive device 102 may be further configured to localize the neighboring organ 114B based on the generated second region in the test video frame. The generated second region may be the neighboring organ 114B. The accuracy of localization of the neighboring organ 114B may be in accordance with the extent of the anatomical adjacency boundary. Alternatively stated, the strength of anatomical adjacency boundary may provide conditional probability values that indicate a stronger likelihood of anatomical adjacency in patches (of the test video frame), where the internal organ of interest 114A and the neighboring organ 114B share a common boundary. The anatomical adjacency boundary between the internal organ of interest 114A and the neighboring organ 114B may be computed based on the generated first localization likelihood values and the generated second localization likelihood values. In accordance with an embodiment, the extent of the anatomical adjacency boundary may be maximum when the degree of correlation between the generated first localization likelihood values and the generated second localization likelihood values is maximum. The localization of the neighboring organ 114B may further aid in localization of the internal organ of interest 114A. The internal organ of interest 114A may be localized post the localization of the neighboring organ 114B, sequentially. In accordance with an embodiment, the internal organ of interest 114A and the neighboring organ 114B may also be localized concurrently in the test video frame.

In accordance with an embodiment, the localization of the internal organ of interest 114A within the body of the human subject 112 may be executed further based on supplemental information for the generated first region. The supplemental information may include at least a set of markers assigned at a contour of the generated first region of the internal organ of interest 114A. In accordance with an embodiment, the surgical assistive device 102 may be further configured to assign the set of markers, at the contour of the generated first region of the internal organ of interest 114A, in the test video frame and different test video frames that are a part of the captured sequence of video frames received as a continuous video feed from the surgical image capture device 104. Also, in some cases, the surgical assistive device 102 may be configured to assign a set of markers different from the set of markers for the internal organ of interest 114A, at the contour of the generated second region of the neighboring organ 114B. Additionally, the surgical assistive device 102 may be further configured to overlay, at the display device 108 associated with the surgical assistive device 102, the supplemental information on the captured sequence of video frames displayed as a continuous feed, in real time or near-real time. The captured sequence of video frames displayed as a continuous feed may be captured via the surgical image capture device 104.

In accordance with an embodiment, the surgical assistive device 102 may be further configured to compare a region (in the test video frame) that depicts the first localization likelihood values for the internal organ of interest 114A with the generated first region in the test video frame. A difference in region occupied by the internal organ of interest 114A may be determined by the surgical assistive device 102, based on comparison of the generated first region and a region in the test video frame based on the first localization likelihood values. As an example, patches in the test video frame that exhibit a texture different from that in the extracted training patches for the internal organ of interest 114A, may cause the conditional probability values (or first likelihood values) for such patches to be lower than patches that exhibit expected textures. Therefore, in such cases, although such patches are part of the regions occupied by the internal organ of interest 114A in the test video frame, however, due to lower likelihood values (appearance), only a portion of the patches may be considered a part of the region occupied by the internal organ of interest 114A in the test video frame. Also, the first region (obtained based on integration of segmented regions) for the internal organ of interest 114A may be much more accurate than that identified through the first likelihood values. Such accuracy may be obtained due to involvement of mutual anatomical adjacency (or other edge information) to further classify patches (or regions) in the test video frame that maps to the internal organ of interest 114A.

In some embodiments, the surgical assistive device 102 may be further configured to generate instructions to enable navigation of a surgical tool or instrument within the body of the human subject 112 to reach to the first region of the internal organ of interest 114A by the surgeon 116 during surgery. Although, the disclosure describes the localization of the internal organ of interest 114A based on mutual anatomical adjacency with the neighboring organ 114B in a test video frame selected from a continuous feed of video taken during intraoperative state of the human subject 112. However, the disclosure may not be so limited and the localization of the internal organ of interest 114A may be done based on mutual anatomical adjacency with different neighboring organs in same or different test video frames.

Figure 2:
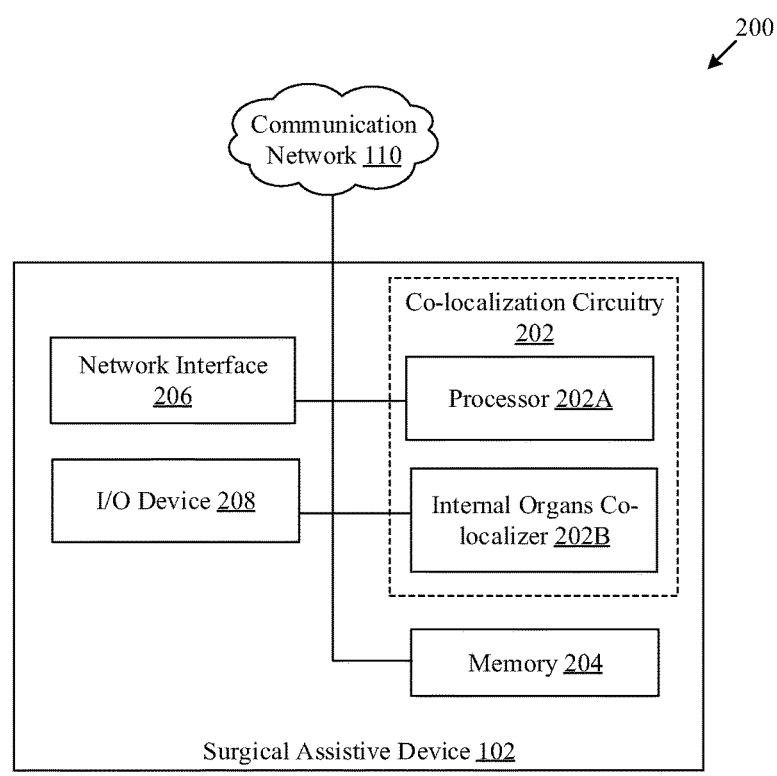
FIG. 2 illustrates a block diagram of an exemplary surgical assistive device for co-localization of an internal organ of interest and a neighboring organ based on images obtained during surgery, in accordance with an embodiment of the disclosure.

FIG. 2 illustrates a block diagram of an exemplary surgical assistive device for co-localization of an internal organ of interest and a neighboring organ based on images obtained during surgery, in accordance with an embodiment of the disclosure. FIG. 2 is explained in conjunction with elements from FIG. 1. With reference to FIG. 2, there is shown a block diagram 200 of the surgical assistive device 102. The surgical assistive device 102 may include one or more circuits, such as co-localization circuitry 202, a memory 204, a network interface 206, one or more input/output (I/O) devices, such as an I/O device 208. The co-localization circuitry 202 may include a processor 202A, and an internal organs co-localizer 202B. The I/O device 208 may be communicatively coupled to the surgical image capture device 104 and the display device 108, via the communication network 110. Alternatively, the I/O device 208 may be directly coupled to the surgical image capture device 104 and the display device 108 through dedicated buses and/or channels. The co-localization circuitry 202 may be communicatively coupled to the memory 204, the network interface 206, and the I/O device 208. The network interface 206 may communicate with the one or more medical data server 106s, such as the medical data server 106, via the communication network 110 under the control of the co-localization circuitry 202.

The co-localization circuitry 202 may comprise suitable logic, circuitry, and interfaces that may be configured to localize the internal organ of interest 114A and the neighboring organ 114B of the human subject 112. The co-localization may be done based on implementation a Bayesian inference/co-inference framework on a plurality of video frames captured by the surgical image capture device 104 (e.g., an imaging laparoscope). The Bayesian inference/co-inference framework may be implemented by different components of the co-localization circuitry 202, using different image processing techniques. The co-localization circuitry 202 may be implemented based on a number of processor technologies known in the art. Examples of processor technologies to implement the co-localization circuitry 202 may be an x86-based processor, x86-64-based processor, a Reduced Instruction Set Computing (RISC) processor, an Application-Specific Integrated Circuit (ASIC) processor, a Complex Instruction Set Computing (CISC) processor, a central processing unit (CPU), an Explicitly Parallel Instruction Computing (EPIC) processor, a Very Long Instruction Word (VLIW) processor, and/or other processors or circuits.

The processor 202A may comprise suitable logic, circuitry, and interfaces that may be configured to execute instructions stored in the memory 204. Examples of the processor 202A may be an x86-based processor, x86-64-based processor, an ASIC processor, a CPU, an EPIC processor, a VLIW processor, and/or other processors or circuits.

The internal organs co-localizer 202B may comprise suitable logic, circuitry, and interfaces that may be configured to localize the internal organ of interest 114A along with the neighboring organ 114B in a test video frame. The test video frame may be captured, using the surgical image capture device 104, from inside the body of the human subject 112 during the surgery. For example, an imaging laparoscope that is inserted in an abdominal region of the body and captures a continuous feed of video frames that may include the internal organ of interest 114A along with one or more neighboring organs. The internal organ co-localizer 202B may be implemented based on a number of processor technologies known in the art. Examples of the processor technologies to implement the internal organ co-localizer 202B may be an x86-based processor, x86-64-based processor, a RISC processor, an ASIC processor, a CISC processor, a CPU, an EPIC processor, a VLIW processor, and/or other processors or circuits.

The memory 204 may comprise suitable logic, circuitry, and/or interfaces that may be configured to store a machine code and/or a set of instructions executable by the co-localization circuitry 202. The memory 204 may be configured to store training data related to appearance (e.g., texture, color, etc.) of the internal organ of interest 114A and the neighboring organ 114B. The data may be extracted from the medical data server 106 and stored at the memory 204. The memory 204 may be further configured to store a sequence of video frames captured by the surgical image capture device 104. The memory 204 may be further configured to store data associated with operating systems and related applications. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The network interface 206 may comprise suitable logic, circuitry, and interfaces that may be configured to communicate with the surgical image capture device 104, the medical data server 106, and/or the display device 108, via the communication network 110 (as shown in FIG. 1). The network interface 206 may implement known technologies to support wired or wireless communication of the surgical assistive device 102 with the communication network 110. The network interface 206 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer.

The I/O device 208 may comprise suitable logic, circuitry, and interfaces that may be configured to receive an input from and provide an output to a user based on the received input from the user. The I/O device 208 may receive an input from the surgical image capture device 104 and provide an output to the display device 108 that may include visualizations and other data to render interactivity and/or other services to the user. Such visualizations and other data may be rendered in conjunction with various inputs from the surgical assistive device 102. Examples of the input devices may include, but are not limited to, a touch screen, a camera (e.g., the surgical image capture device 104), a keyboard, a mouse, a joystick, a microphone, a motion sensor, a light sensor, and/or a docking station. Examples of the output devices may include, but are not limited to, a projector screen, a speaker, and/or a display device (e.g., the display device 108). Various operations of the different components of the surgical assistive device 102, may be further understood in details, for example, from FIGS. 3A to 3C.

Figure 3A:
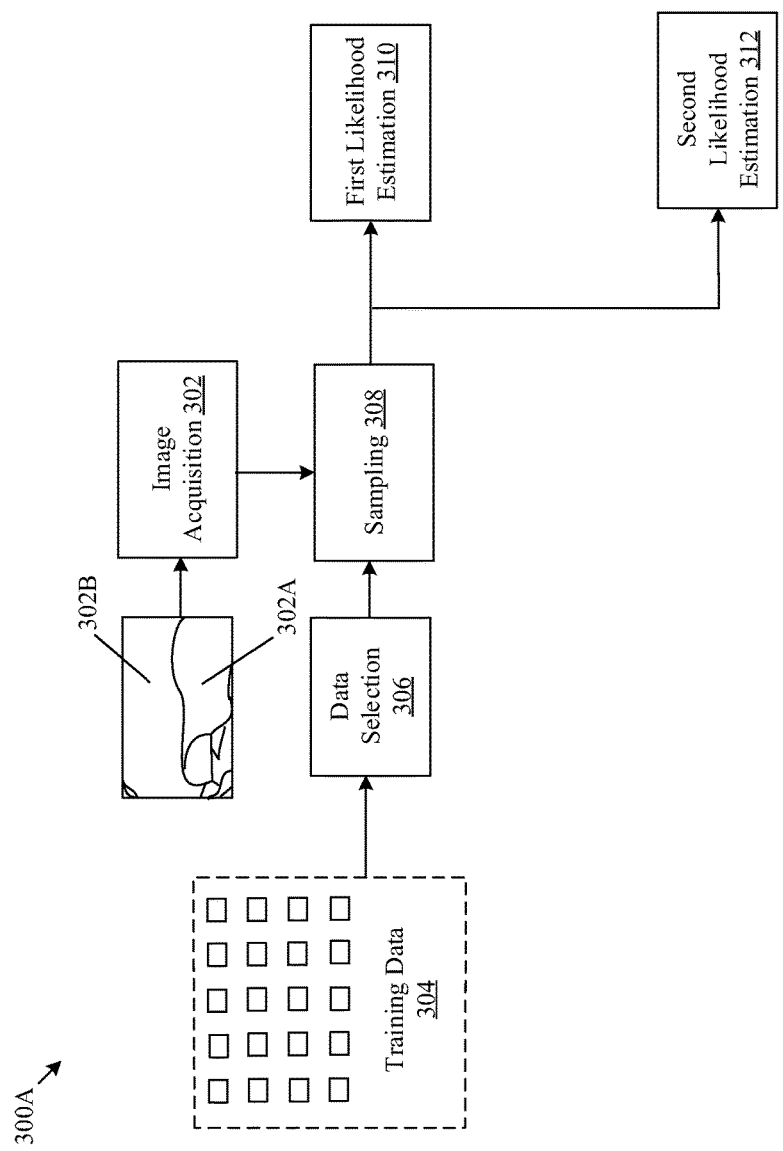
FIG. 3A illustrates a processing pipeline to depict generation of first localization likelihood values for an internal organ of interest and second localization likelihood values for a neighboring organ having an anatomical adjacency with the internal organ of interest, in accordance with an embodiment of the disclosure.
Figure 3B:
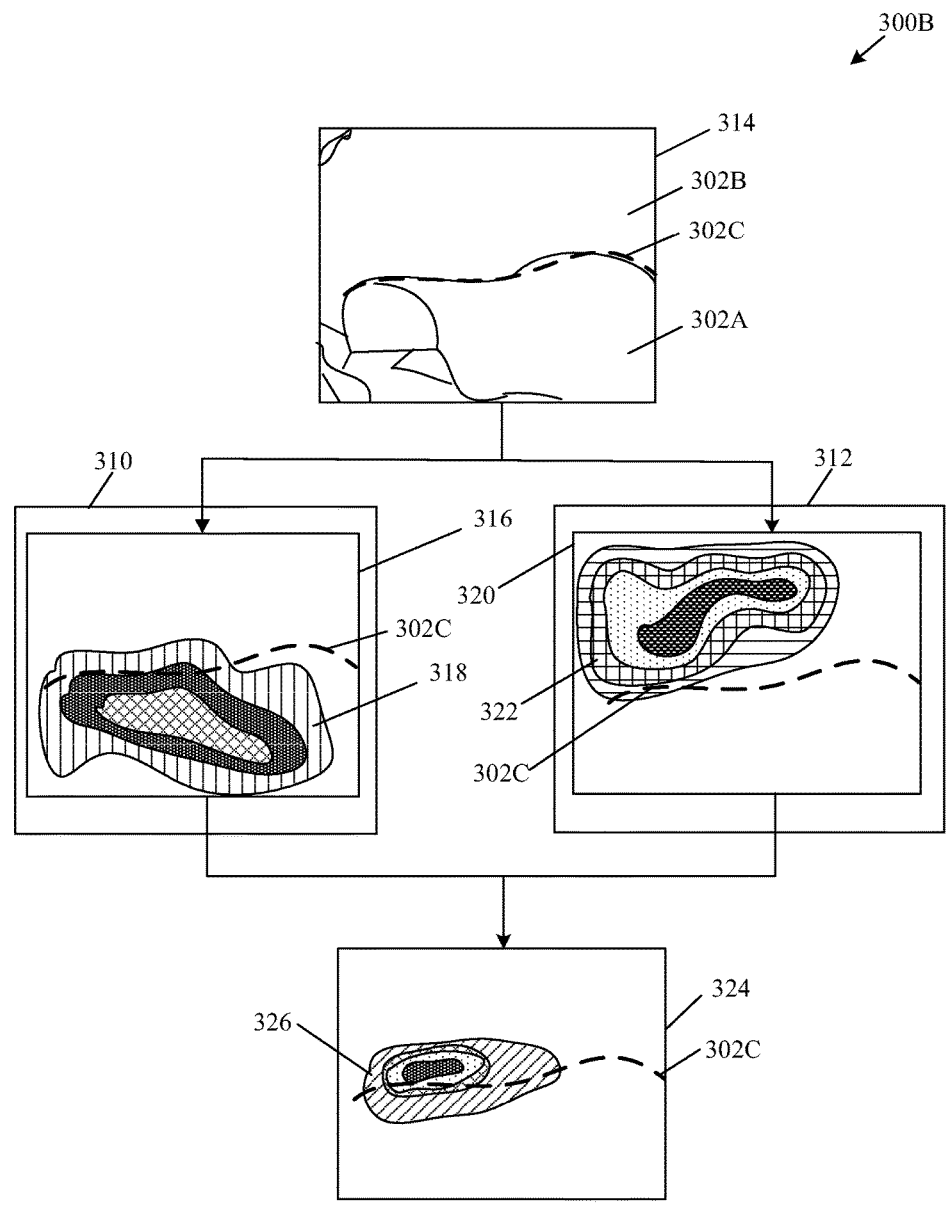
FIG. 3B illustrates an exemplary scenario for determination of an anatomical adjacency boundary between an internal organ of interest and a neighboring organ in a selected test video frame, in accordance with an embodiment of the disclosure.

FIG. 3A illustrates a processing pipeline to depict generation of first localization likelihood values for an internal organ of interest and second localization likelihood values for a neighboring organ having an anatomical adjacency with the internal organ of interest in a selected test video frame, in accordance with an embodiment of the disclosure. FIG. 3A is explained in conjunction with elements from FIGS. 1 and 2. In FIG. 3A, there is shown a processing pipeline 300A that depicts different operations 302 to 312 for generation of first localization likelihood values for an internal organ of interest and second localization likelihood values for a neighboring organ having an anatomical adjacency with the internal organ of interest. The internal organ of interest 114A may be an abdominal organ, such as stomach and the neighboring organ 114B may also be an abdominal organ, such as liver. Test images for the stomach and the liver may be received from the surgical image capture device 104 during intraoperative state of the human subject 112 in surgery, for example, in Hepatectomy (for liver) or Gastrectomy (for stomach). A test video frame and training data may be received at operations 306 and 308, respectively, in the processing pipeline 300A.

At 302, an image acquisition from inside of the body of a subject (e.g., the human subject 112) may be executed. The surgical image capture device 104 may be inserted into the human subject 112 to capture a sequence of video frames (i.e., the image acquisition) using the surgical image capture device 104, from inside of the body of the subject (e.g., the human subject 112). The captured sequence of video frames may depict two or more internal organs of the human subject 112. The I/O device 208 may be configured to receive the captured sequence of video frames from the surgical image capture device 104. As the captured sequence of video frames may include different internal organs of the human subject 112, certain video frames may be selected from the captured sequence of video frames for further processing to avoid selection of unwanted video frames, where a view of the stomach and the liver may not be present or a quality score of the view may be less than a threshold quality as a result of presence of other anatomical portions (of no interest to the surgeon 116). A test video frame may be selected by the surgical image capture device 104. The test video frame may depict abdominal organs (e.g., stomach 302A and liver 302B) or a portion of the abdominal organs of the subject (e.g., the human subject 112). One of the abdominal organs, i.e., the stomach 302A may need to be localized based on localization of liver 302B (neighboring to the stomach 302A) and a likelihood of mutual anatomical adjacency between the stomach 302A and the liver 302B, in the test video frame. As an example, the anatomical adjacency for the liver 302B may be described verbally as follows: "the liver 302B is located in an upper right-hand portion of the abdominal cavity, beneath the diaphragm and on top of the stomach 302A. In quantitative terms, the anatomical adjacency may indicate relative coordinates and relative position of the liver 302B in relation to the stomach 302A in the test video frame.

The view of the body in the test video frame may include posterior portions (or in entirety) of various anatomical structures (such as abdominal organs), blood spots, tumors, and the like. The co-localization circuitry 202 may be configured to select the test video frame from the received sequence of video frames. The selection of the test video frame may be done based on an area occupied by the stomach 302A and the liver 302B in the test video frame. The test video frame may be further selected when the area occupied by the stomach 302A and the liver 302B in the test video frame is greater than a threshold area.

At 304, training data may be received by the surgical image capture device 104 from the medical data server 106. The training data may include at least a set of training patches that represents appearance of the stomach 302A and at least a set of training patches that represents appearance of the liver 302B. In accordance with the exemplary scenario, the training data may further include a first set of training patches of the internal organ of interest 114A and a second set of training patches of the neighboring organ 114B. The first set of training patches of the training data may relate to appearance of the internal organ of interest 114A and the second set of training patches of the training data may relate to appearance of the neighboring organ 114B. The first set of training patches of the training data may relate to an appearance of the internal organ of interest 114A and the second set of training patches of the training data may relate to an appearance of the neighboring organ 114B. The training data may include imaging data of the internal organ of interest 114A and the neighboring organ 114B of different human subjects (e.g., a large sample data). In accordance with an embodiment, the medical data server 106 may be configured to provide pre-stored versions of the training data to the surgical assistive device 102, via the communication network 110.

At 306, selection of the training data related to the stomach 302A and the liver 302B may be executed. The stomach 302A may be an internal organ of interest and the liver 302B may be a neighboring organ of the human subject 112. Data selection may be done to train a learning engine (not shown) for a prior appearance of the stomach 302A and the liver 302B. The processor 202A may be configured to extract the training data from the memory 204 or the medical data server 106. The first set of training patches and the second set of training patches from the training data may also include the patches extracted from multi-modal images, for example, images taken from the Magnetic Resonance Imaging (MRI), the Computed Tomography (CT), the Positron emission tomography (PET), the Fluid-attenuated inversion recovery (FLAIR) and the Magnetic Resonance Angiography (MRA) based medical imaging techniques for same or different human subjects.

At 308, sampling of the training data may be done. The processor 202A may be configured to sample the training data. The training data may be sampled by extraction of the first set of training patches and the second set of training patches from the training data that corresponds to a stomach and a liver, respectively, by a random sampling technique. The test video frame may be a high-resolution video frame of the inside of the body. Further, the set of training patches in training data may be large in number, for example, taken from thousands of sample images. The high resolution video frames and the large number of training data may increase a computational load on the processor 202A. Therefore, to decrease the computational load on the processor 202A, a random sampling technique may be performed. The random sampling technique may be Monte Carlo sampling. However, other sampling techniques may also be used without limiting the scope of the disclosure. The processor 202A may be further configured to utilize the received set of training patches for generation of first localization likelihood values for the stomach 302A and second localization likelihood values for the liver 302B.

At 310, the second localization likelihood values for the stomach 302A may be generated. The internal organs co-localizer 202B may be configured to receive the first set of training patches after the sampling technique is executed on the training patches. In accordance with an embodiment, the size of the training patches may be defined to reduce computational load, for example, a patch of "128 by 128" pixels may be selected. The localization of the stomach 302A may be modelled probabilistically by generation of the first localization likelihood values for the stomach 302A. The internal organs co-localizer 202B may be configured to compare each extracted training patch of the first set of training patches with each test patch in the set of test patches of the test video frame to generate the first localization likelihood values for the stomach 302A. Alternatively stated, the internal organ co-localizer 202B may determine a conditional probability value that indicates (on a normalized scale between 0 and 1) an extent by which a test patch (from the test video frame) matches the appearance of training patches extracted from the training data.

The internal organs co-localizer 202B may be configured to generate the first localization likelihood values for the stomach 302A (i.e., the internal organ of interest 114A) in the test video frame. The generation of the first localization likelihood values for the stomach 302A may be based on the test video frame and the sampled training patches of the training data for the stomach 302A. The generation of the first localization likelihood values for the stomach 302A may be based on prior information that how the stomach 302A appears in terms of texture (appearance parameter). However, other appearance parameters may also be used without limiting the scope of the disclosure.

In accordance with an embodiment, the first localization likelihood values for the stomach 302A may also be calculated in terms of probability. The first localization likelihood values may correspond to a conditional probability distribution that indicates a likelihood of presence of the stomach 302A in different test patches of the test video frame, for a known (or pre-estimated) likelihood of presence of the stomach 302A in the training patches. The conditional probability distribution for the first localization likelihood values may also indicate a degree of match (or similarity), in terms of appearance (e.g., texture), of the stomach 302A in the test video frame with the extracted training patches that represents a given appearance of the stomach 302A. Therefore, the conditional probability distribution for appearance-based localization likelihood for the stomach 302A in a test video frame, may be represented by $P(S_y|A_y)$, where $P(S_y|A_y)$ is a conditional probability that indicates an appearance likelihood of the stomach 302A (represented by S at y coordinate in the test video frame) for a given appearance of the stomach 302A in the training patches.

At 312, the second localization likelihood values for the liver 302B may be generated. The internal organs co-localizer 202B may be configured to receive the second set of training patches after the sampling technique performed on the training patches. In accordance with an embodiment, the size of the training patches may be defined to reduce computational load, for example, a patch of "128 by 128" pixels may be selected. The localization of the liver 302B may be modelled probabilistically by generation of the second localization likelihood values for the liver 302B. In accordance with an embodiment, the internal organs co-localizer 202B may be configured to compare each extracted training patch of the second set of training patches with each test patch in the set of test patches of the test video frame to generate the second localization likelihood values for the liver 302B.

The internal organs co-localizer 202B may be configured to generate the second localization likelihood values for the liver (i.e., the neighboring organ 114B) in the test video frame. The generation of the second localization likelihood values for the liver 302B may be based on the test video frame and the sampled training patches of the training data for the liver 302B. The generation of the second localization likelihood values for the liver 302B may be based on prior information about appearance of the liver 302B in terms of an appearance parameter (e.g., texture). However, other appearance parameters may also be used without limiting the scope of the disclosure. As an example, patches that depict a portion of the liver 302B have generally a fine texture with a dark tint and patches that depict a portion of the stomach 302A have generally visible veins with a lighter tint.

In accordance with an embodiment, the second localization likelihood values for the liver 302B may also be calculated in terms of probability. The second localization likelihood values may correspond to a conditional probability distribution for localization of the liver 302B, given that the appearance of the liver 302B in the set of training patches. The conditional probability distribution of the liver 302B may be represented by $P(L_x|A_x)$, where $P(L_x|A_x)$ is a conditional probability that indicates an appearance likelihood of the liver 302B (represented by "L" at "x" coordinate in the test video frame) for a given appearance of the liver 302B in the training patches.

FIG. 3B illustrates an exemplary scenario for determination of an anatomical adjacency boundary between an internal organ of interest and a neighboring organ in the selected test video frame, in accordance with an embodiment of the disclosure. FIG. 3B is explained in conjunction with elements from FIGS. 1, 2 and 3A. In FIG. 3B, there is shown an exemplary scenario 300B for determination of an anatomical adjacency boundary between the internal organ of interest 114A and the neighboring organ 114B in a test video frame 314.

As shown, the test video frame 314 includes a test patch that may either depict a portion of the stomach 302A, a portion of the liver 302B, a portion of other neighboring organs, or a combination thereof. The internal organs co-localizer 202B may be configured to generate first localization likelihood values for the portion of the stomach 302A depicted in the test video frame 314. In the exemplary scenario 300B, the first localization likelihood values are visually depicted by a shaded region 318 in a frame 316. The shaded region 318 indicates a region in the test video frame 314 where the likelihood of localization of the stomach 302A is maximum. The likelihood may itself vary at different points on the shaded region 318, for example, higher likelihood near the center and lower near the edges of the shaded region 318.

Similarly, the internal organs co-localizer 202B may be configured to generate second localization likelihood values for the portion of the liver 302B depicted in the test video frame 314. In the exemplary scenario 300B, the second localization likelihood values are visually depicted by a shaded region 322 in a frame 320. The shaded region 322 indicates a region in the test video frame 314 where the likelihood of localization of the liver 302B is maximum. The likelihood may itself vary at different points on the shaded region 322, for example, higher likelihood near the center and lower near the edges of the shaded region 322.

The internal organs co-localizer 202B may be configured to compute an anatomical adjacency boundary 302C (represented by thick dashed lines in FIG. 3B) between the stomach 302A and the liver 302B. When the training data is sampled by using a random sampling technique, such as, Monte Carlo sampling as described in FIG. 3A, the number of training patches of the training data must be large in number. Otherwise, small number of training patches (i.e., less than a defined number) for the training data may result in large interpolation errors that may be a weakness of the random sampling technique. However, the random sampling may be a pertinent step to save time for calculations related to localization of the stomach 302A and the liver 302B. However, the random sampling may cause sub-region errors that may result in incorrect classification of the anatomical adjacency boundary 302C. An overlapped map 324 that depicts a likelihood of the anatomical adjacency boundary 302C between the stomach 302A and the liver 302B is shown by a shaded region 326 in the overlapped map 324.

For relative accurate classification of the stomach 302A and the liver 302B, the anatomical adjacency boundary 302C (also represented by thick dashed lines) may be computed from a product of the generated first localization likelihood values (represented by shaded region 318) for the stomach 302A and the generated second localization likelihood values (represented by the shaded region 322) for the liver 302B. The generated first localization likelihood values may be represented as $P(L_x|A_x)$ and the generated second localization likelihood values may be represented by $P(S_y|A_y)$. The product of $P(L_x|A_x)$ and $P(S_y|A_y)$, may be depicted by the shaded region 326, which may indicate an extent of anatomical adjacency boundary 302C between the stomach 302A and the liver 302B.

The internal organs co-localizer 202B may be configured to determine an extent of the anatomical adjacency boundary 302C between the stomach 302A and the liver 302B in the test video frame 314. The determination of the extent of the anatomical adjacency boundary 302C may be based on a degree of correlation between the generated first localization likelihood values and the generated second localization likelihood values. In accordance with an embodiment, the extent of the anatomical adjacency boundary 302C may be represented by a region (e.g., the shaded region 326) in the test video frame 314 that includes test patches for which a correlation of the first localization likelihood values and the second localization likelihood values may lie above a threshold likelihood value. In accordance with an embodiment, the internal organs co-localizer 202B may be further configured to utilize the computed anatomical adjacency boundary 302C for a precise classification of the stomach 302A from the liver 302B when the extent of the computed anatomical adjacency boundary 302C is maximum. The region 326 may signify that a strength of overlapping between the shaded region 318 and the shaded region 322 is maximum in the overlapped map 324.

Figure 3C:
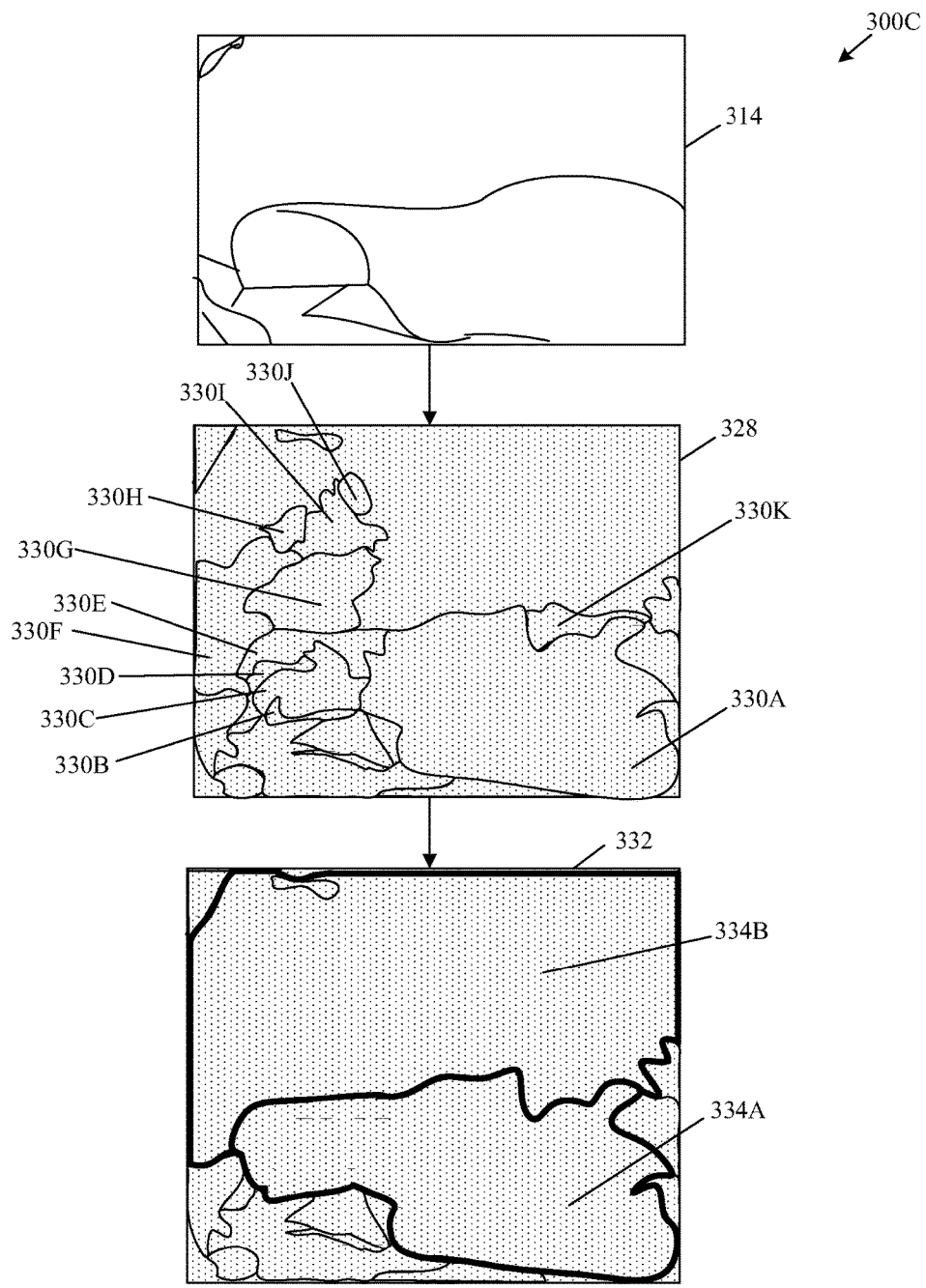
FIG. 3C illustrates an exemplary scenario for region integration and localization in a selected test video frame for an abdominal organ and a neighboring organ of a subject, in accordance with an embodiment of the disclosure.

FIG. 3C illustrates an exemplary scenario for region integration and localization of an internal organ of interest and a neighboring organ in a test video frame, in accordance with an embodiment of the disclosure. FIG. 3C is explained in conjunction with elements from FIGS. 1, 2, 3A and 3B. With reference to FIG. 3C, there is shown a scenario 300C for localization of stomach and liver in the test video frame 314 based on a segmented frame 328 and an integrated frame 332.

The test video frame 314 may be segmented into a plurality of regions that are part of the segmented frame 328. The internal organs co-localizer 202B may be configured to segment the test video frame 314 into the plurality of regions, such as a region 330A, a region 330B, a region 330C, a region 330D, a region 330E, a region 330F, a region 330G, a region 330G, a region 330H, a region 330I, a region 330J, and a region 330K. In segmentation, pixels in the test video frame 314 having similar characteristics (e.g., based on k-means clusters, thresholding, etc.) may be clustered into a single region.

The internal organs co-localizer 202B may be configured to generate a first region 334A that indicates the stomach 302A (shown in FIG. 3B), as shown in the segmented frame 332. The first region 334A may be generated based on integration of a first set of regions (i.e. the region 330A, the region 330B, the region 330C, the region 330D, and the region 330E) from the plurality of regions in the segmented frame 328. The region 330A, the region 330B, the region 330C, the region 330D, and the region 330E may correspond to samples for which the likelihood of localization of the stomach 302A is maximum. The first set of regions may be integrated in order to identify a region where the likelihood of localization of the stomach 302A in the test video frame 314 is maximum. Also, the first region (for the stomach 302A) may further correspond to a localization parameter ($S_Y$) that indicates a maximum posterior localization of the stomach 302A. The maximum posterior localization (in terms of the localization parameter ($S_Y$) is given by equation (1), as follows:

$$S_Y = \underset{S_Y}{\operatorname{argmax}} P(S_Y \mid L_X, A_X, A_Y, J_{LS}(X, Y)) = \underset{S_Y}{\operatorname{argmax}} P(S_Y \mid L_X, J_{LS}) \quad (1)$$

Where argmax (also referred to as argument of maxima) represents a set of samples (i.e. test patches from the test video frame 314) for which the localization parameter ($S_Y$) in the conditional probability distribution ($P(S_Y|L_X,J_{LS})$) achieves a maximum value. The set of samples when represented on the integrated frame 330, may constitute the first region. Where $L_X$ represents a localization parameter for the liver 302B, $J_{LS}(X,Y)$ or $J_{LS}$ represents the anatomical adjacency boundary 302C (also referred to as likelihood of anatomical adjacency between the stomach 302A and the liver 302B in different samples (i.e. test patches of the test video frame 314).

The first set of regions may be integrated based on the conditional probabilistic distribution ($P(S_Y|L_X,J_{LS})$) for the localization parameter ($S_Y$) of the stomach 302A in the test video frame 314 with respect to the anatomical adjacency boundary 302C ($J_{LS}$) and the localization parameter ($L_X$) for the liver 302B. $P(S_Y|L_X,J_{LS})$ may also represent a probability distribution, where each probability value over a sample (I.e. a test patch) may indicate a likelihood of presence of a portion of the stomach 302A given a likelihood of the presence of a portion of the liver 302B and a likelihood of presence of the anatomical adjacency boundary 302C in the sample. In accordance with an embodiment, the conditional probabilistic distribution ($P(S_Y|L_X,J_{LS})$) may be also represented by equation (2) using Bayes' Theorem, as follows:

$$P(S_Y \mid L_X, J_{LS}) = \frac{P(J_{LS} \mid L_X, S_Y) \times P(L_X, S_Y)}{P(L_X, J_{LS})} \quad (2)$$

where ($L_X,J_{LS}$) represents a joint probability distribution over a set of samples (i.e. set of test patches from the test video frame 314), which indicates a likelihood for a localization parameter ($L_X$) of the liver 302B and a likelihood of presence of the anatomical adjacency boundary 302C ($J_{LS}$); where the likelihood, $P(J_{LS}|L_X,S_Y)$ represents a conditional probability distribution over a set of samples. The conditional probability distribution may indicate, for each sample, a likelihood of presence of anatomical adjacency boundary 302C ($J_{LS}$) given a likelihood of presence of the stomach 302A and the liver 302B; and where $P(L_X,S_Y)$ represents a joint likelihood (also referred as joint probability) that a sample (or the entire test video frame 314) of the test video frame 314 may capture a portion of the stomach 302A and the liver 302B. For the entire test video frame 314, the $P(L_X,S_Y)$ may be assumed to be constant, such as "1" as only those test video frames may be captured or selected, which depict both the stomach 302A and the liver 302B. $P(L_X,S_Y)$ may also referred to as a prior belief of a surgeon (e.g., the surgeon 116) prior to performing the surgery. The prior belief may represent a belief of the surgeon 116 for a location of the liver 302B and the stomach 302A in an abdominal cavity before an incision is made in the abdominal wall during surgery.

In accordance with an embodiment, when prior belief is assumed uniform, the probability distribution ($P(L_X,S_Y)$) may be constant for all the estimated values for the localization parameter ($S_Y$) of the stomach 302A. The location of a peak of a curve for the probability distribution ($P(L_X,S_Y)$) with uniform prior belief may be called as the maximum likelihood estimate (MLE) of the localization parameter ($S_Y$) of the stomach 302A. The result of use of uniform prior belief may be similar to a statistical estimate of the estimated values for the localization parameter ($S_Y$) of the stomach 302A. In some cases, a uniform prior belief may also show that every possible outcome may be equally likely, which is rarely the case. The peak of the posterior conditional probability distribution is also known as a maximum posteriori estimate or MAP. The MAP may facilitate the surgeon 116 to make a confident estimate.

In accordance with an embodiment, the internal organs co-localizer 202B may be further configured to integrate a second set of regions (i.e. the region 330F, the region 330G, the region 330H, the region 330I, and the region 330J, and the region 330K) into a second region 334B for the liver 302B, as shown in the segmented frame 332. The integration of the second set of regions may be done based on the generated second localization likelihood values for the liver 302B. Regions from the plurality of regions that have greater appearance likelihood (as represented by the second localization likelihood values) may constitute the second set of regions. The generated second localization likelihood values for the liver 302B may be represented as $P(L_X|A_X)$. The plurality of regions (obtained after segmentation) may further include regions that may not be integrated into either of the first region 334A or the second region 334B (as shown in the segmented frame 332). Such regions are not selected for integration as the localization likelihood (represented by equation (1) and equation (2) for such regions are below a threshold value of likelihood.

The internal organs co-localizer 202B may be configured to localize the liver 302B based on the generated second region 334B, in accordance with the extent of the anatomical adjacency boundary 302C (as represented by $P(S_Y|A_Y) \times P(L_X,A_X)$). In accordance with an embodiment, the internal organs co-localizer 202B may be configured to localize the stomach 302A that may be the generated first region 334A, in accordance with the extent of the anatomical adjacency boundary 302C (as represented by $P(S_Y|A_Y) \times P(L_X,A_X)$). In accordance with an embodiment, the internal organs co-localizer 202B may be configured to assign supplemental information, such as a set of markers, at the contour of the generated second region 334B for the liver 302B and the generated first region 334A for the stomach 302A, in the test video frame 314 and different test video frames that are a part of the captured sequence of video frames. In certain embodiments, the internal organs co-localizer 202B may be configured to overlay, at a display device 108 associated with the surgical assistive device 102, the supplemental information on the captured sequence of video frames displayed as a continuous feed, in real time or near-real time.

In accordance with an embodiment, the internal organs co-localizer 202B may be configured to compare a region in the test video frame 314 that depicts the first localization likelihood values for the stomach 302A with the generated first region 334A. The internal organs co-localizer 202B may be further configured to identify a difference in the region occupied by the stomach 302A by comparison in the generated first region 334A and a region in the test video frame 314 that depicts the first localization likelihood values for the stomach 302A. In some embodiments, the internal organs co-localizer 202B may be further configured to generate instructions to enable navigation of a surgical tool or instrument within the body of the subject (e.g., the human subject 112) to reach to the first region 334A of the stomach 302A, within the body of the subject.

Figure 4A:
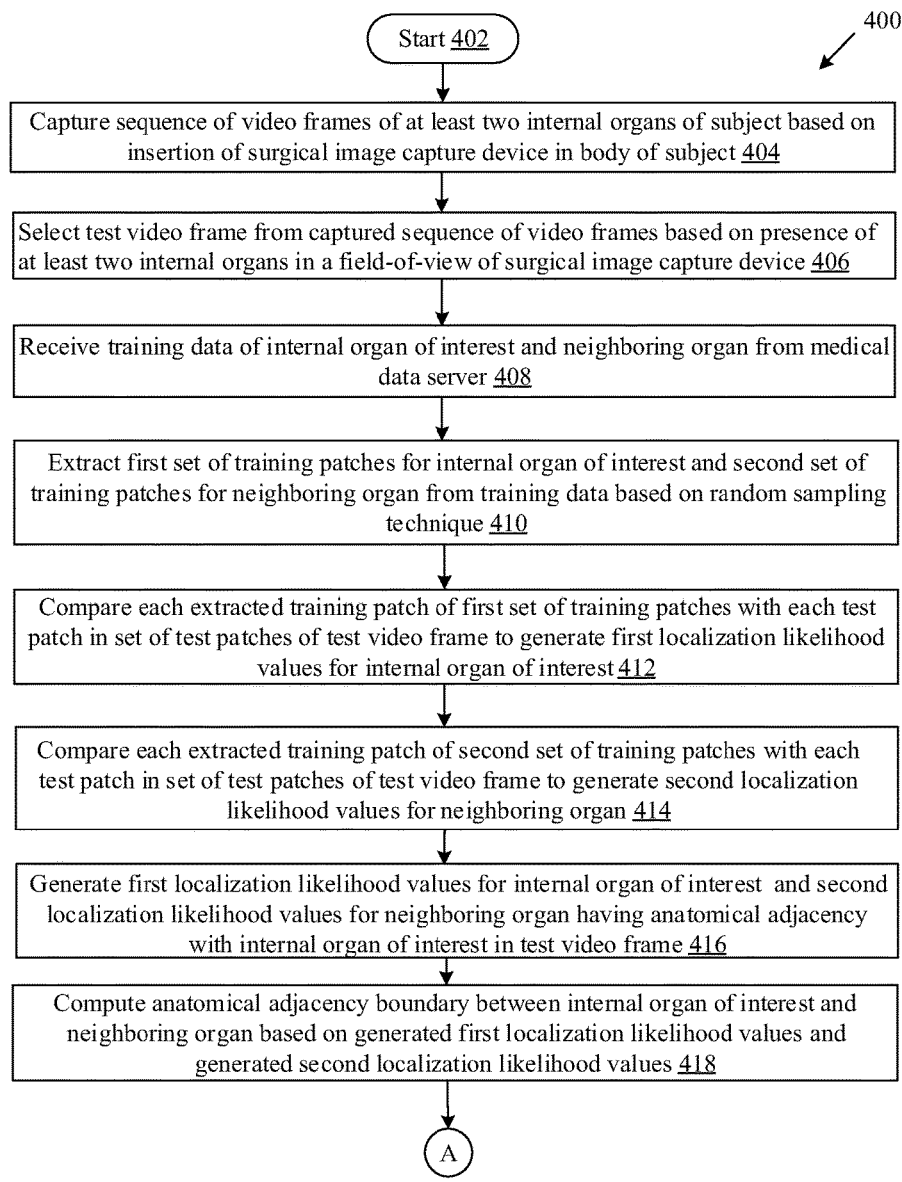
FIGS. 4A, 4B, and 4C, collectively depicts a flow chart that illustrates exemplary operations for co-localization of an internal organ of interest and a neighboring organ of a subject based on images obtained during surgery, in accordance with an embodiment of the disclosure.
Figure 4B:
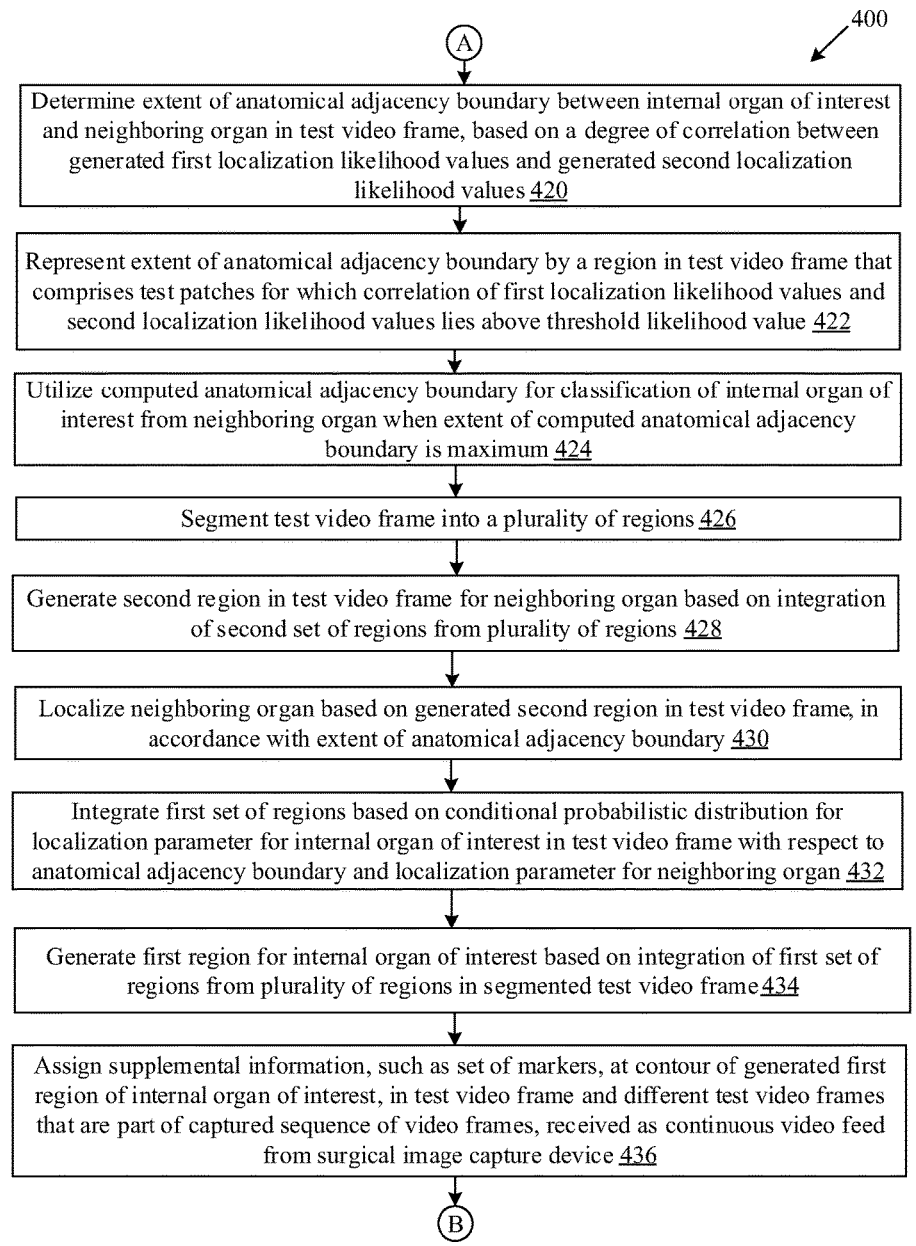
Figure 4C:
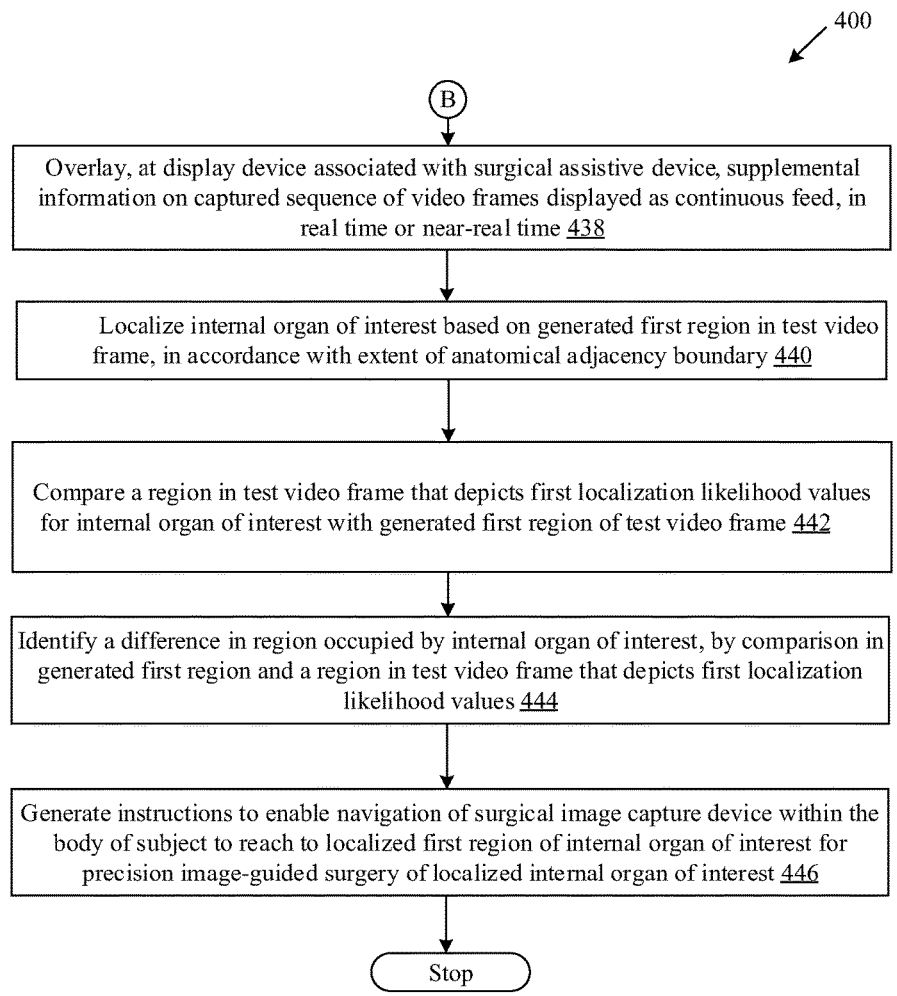

FIGS. 4A, 4B, and 4C, collectively depicts a flowchart that illustrates exemplary operations for co-localization of an internal organ of interest and a neighboring organ of a subject based on images obtained during surgery, in accordance with an embodiment of the disclosure. With reference to FIGS. 4A, 4B, and 4C, there is shown a flowchart 400. The flowchart 400 is described in conjunction with elements from FIGS. 1, 2, and 3A to 3C. The method, in accordance with the flowchart 400, may be implemented in the surgical assistive device 102. The method starts at 402 and proceeds to 404.

At 404, a sequence of video frames of one or more internal organs of a subject may be captured, based on insertion of the surgical image capture device 104 in the body of a subject. The surgical image capture device 104 may be configured to capture a sequence of video frames of one or more internal organs of a subject, based on insertion of the surgical image capture device 104 in the body of a subject (e.g., the human subject 112).

At 406, a test video frame from the captured sequence of video frames may be selected, based on presence of at least two organs, i.e., the internal organ of interest 114A and the neighboring organ 114B in a field-of-view of surgical image capture device 104. The processor 202A may be configured to select the test video frame from the captured sequence of video frames, based on presence of at least two organs, i.e., the internal organ of interest 114A and the neighboring organ 114B, in the test video frame.

At 408, training data associated with the internal organ of interest 114A and the neighboring organ 114B may be received from the medical data server 106. The memory 204 may be configured to receive the training data associated with the internal organ of interest 114A and the neighboring organ 114B to generate first localization likelihood values for the internal organ of interest 114A and second localization likelihood values for the neighboring organ 114B. The training data may further include a first set of training patches for generation of a first localization likelihood values of the internal organ of interest 114A and a second set of training patches for generation of a second localization likelihood values for the neighboring organ 114B.

At 410, a first set of training patches for the internal organ of interest 114A and a second set of training patches for the neighboring organ 114B may be extracted from the received training data based on a random sampling technique. The processor 202A may be configured to extract first set of training patches for the internal organ of interest 114A and a second set of training patches for the neighboring organ 114B may be extracted from the received training data based on a random sampling technique.

At 412, each extracted training patch of the first set of training patches may be compared with each test patch in the set of test patches of the test video frame, to generate first localization likelihood values for the internal organ of interest 114A. The processor 202A may be configured to compare each extracted training patch of the first set of training patches with each test patch in the set of test patches of the test video frame, to generate first localization likelihood values for the internal organ of interest 114A.

At 414, each extracted training patch of the second set of training patches may be compared with each test patch in the set of test patches of the test video frame, to generate second localization likelihood values for neighboring organ 114B. The processor 202A may be configured to compare each extracted training patch of the second set of training patches with each test patch in the set of test patches of the test video frame, to generate second localization likelihood values for the neighboring organ 114B.

At 416, first localization likelihood values for the internal organ of interest 114A and second localization likelihood values for the neighboring organ 114B having an anatomical adjacency with the internal organ of interest 114A may be generated in the test video frame. The internal organs co-localizer 202B may be configured to generate the first localization likelihood values for the internal organ of interest 114A and the second localization likelihood values for the neighboring organ 114B.

At 418, the anatomical adjacency boundary between the internal organ of interest 114A and the neighboring organ 114B may be computed based on the generated first localization likelihood values and the generated second localization likelihood values. The internal organs co-localizer 202B may be configured to compute the anatomical adjacency boundary between the internal organ of interest 114A and the neighboring organ 114B based on the generated first localization likelihood values and the generated second localization likelihood values.

At 420, an extent of an anatomical adjacency boundary may be determined between the internal organ of interest 114A and the neighboring organ 114B in the test video frame, based on a degree of correlation between the generated first localization likelihood values and the generated second localization likelihood values. The internal organs co-localizer 202B may be configured to determine the extent of the anatomical adjacency boundary between the internal organ of interest 114A and the neighboring organ 114B in the test video frame, based on a degree of correlation between the generated first localization likelihood values and the generated second localization likelihood values.

At 422, the extent of the anatomical adjacency boundary may be represented by a region in the test video frame that includes test patches, for which a correlation of the first localization likelihood values and the second localization likelihood values lies above a threshold likelihood value. The internal organs co-localizer 202B may be configured to represent the extent of the anatomical adjacency boundary by a region in the test video frame that includes test patches, for which a correlation of the first localization likelihood values and the second localization likelihood values lies above a threshold likelihood value.

At 424, the computed anatomical adjacency boundary may be utilized for a precise classification of the internal organ of interest 114A from the neighboring organ 114B when the extent of the computed anatomical adjacency boundary is maximum. The internal organs co-localizer 202B may be configured to utilize the computed anatomical adjacency boundary for a precise classification of the internal organ of interest 114A from the neighboring organ 114B when the extent of the computed anatomical adjacency boundary is maximum.

At 426, the test video frame may be segmented into a plurality of regions. The internal organs co-localizer 202B may be configured to segment the test video frame into a plurality of regions.

At 428, a second region may be generated in the test video frame for the neighboring organ 114B based on integration of a second set of regions from the plurality of regions. The integration of the second set of regions may be done based on the generated second localization likelihood values for the neighboring organ 114B. The internal organs co-localizer 202B may be configured to generate a second region in the test video frame for the neighboring organ 114B based on integration of a second set of regions from the plurality of regions.

At 430, the neighboring organ 114B may be localized based on the generated second region in the test video frame, in accordance with the extent of the anatomical adjacency boundary. The internal organs co-localizer 202B may be configured to localize the neighboring organ 114B to the generated second region in the test video frame, in accordance with the extent of the anatomical adjacency boundary.

At 432, first set of regions may be integrated based on a conditional probabilistic distribution for a localization parameter for the internal organ of interest 114A in the test video frame with respect to the anatomical adjacency boundary and a localization parameter for the neighboring organ 114B. The internal organs co-localizer 202B may be configured to integrate the first set of regions based on a conditional probabilistic distribution for a localization parameter for the internal organ of interest 114A in the test video frame with respect to the anatomical adjacency boundary and a localization parameter for the neighboring organ 114B.

At 434, a first region may be generated for the internal organ of interest 114A based on the integration of the first set of regions from the plurality of regions in the segmented test video frame. The internal organs co-localizer 202B may be configured to generate the first region for the internal organ of interest 114A based on the integration of the first set of regions from the plurality of regions in the segmented test video frame.

At 436, supplemental information, such as a set of markers, may be assigned at a contour of the generated first region of the internal organ of interest 114A, in the test video frame and different test video frames that are a part of the captured sequence of video frames, received as a continuous video feed from the surgical image capture device 104. The internal organs co-localizer 202B may be configured to assign supplemental information, such as a set of markers, at the contour of the generated first region of the internal organ of interest 114A, in the test video frame and different test video frames that are a part of the captured sequence of video frames, received as a continuous video feed from the surgical image capture device 104.

At 438, the supplemental information may be overlaid on the captured sequence of video frames displayed as a continuous feed, in real time or near-real time at the display device 108 associated with the surgical assistive device 102. The internal organs co-localizer 202B may be configured to overlay, at the display device 108 associated with the surgical assistive device 102, the supplemental information on the captured sequence of video frames displayed as a continuous feed, in real time or near-real time.

At 440, the internal organ of interest 114A may be localized based on the generated first region in the test video frame, in accordance with the extent of the anatomical adjacency boundary. Alternatively stated, the generated first region may be the region of the internal organ of interest 114A. The internal organs co-localizer 202B may be configured to localize the internal organ of interest 114A to the generated first region in the test video frame, in accordance with the extent of the anatomical adjacency boundary.

At 442, a region may be compared in the test video frame that depicts the first localization likelihood values for the internal organ of interest 114A with the generated first region of the test video frame. The internal organs co-localizer 202B may be configured to compare a region in the test video frame that depicts the first localization likelihood values for the internal organ of interest 114A with the generated first region of the test video frame.

At 444, a difference in region occupied by the internal organ of interest 114A may be identified by comparison of the generated first region and a region in the test video frame that depicts the first localization likelihood values. The internal organs co-localizer 202B may be configured to identify a difference in region occupied by the internal organ of interest 114A by comparison of the generated first region and a region in the test video frame that depicts the first localization likelihood values.

At 446, instructions may be generated to enable navigation of a surgical tool or instrument within the body of the human subject 112 to reach to the localized internal organ of interest 114A for precision image-guided surgery of localized internal organ of interest 114A. The internal organs co-localizer 202B may be configured to enable navigation of the surgical instrument within body of the human subject 112 to reach to the localized internal organ of interest 114A for precision image-guided surgery of localized internal organ of interest 114A. Control passes to end.

Certain embodiments of the disclosure may be found in a surgical assistive device e.g., (the surgical assistive device 102) and method for co-localization of an internal organ of interest (e.g., the internal organ of interest 114A) and a neighboring organ (e.g., the neighboring organ 114B) that has an anatomical adjacency with the internal organ of interest of a subject within images (e.g., laparoscopic images) obtained during surgery. Various embodiments of the disclosure may provide a surgical assistive device. The surgical assistive device may include a surgical image capture device (e.g., the surgical image capture device 104) and a co-localization circuitry (e.g., the co-localization circuitry 202) communicatively coupled to the surgical image capture device. The surgical image capture device may be configured to capture a sequence of video frames. The sequence of video frames of an internal organ of interest (e.g., the internal organ of interest 114A) and at least one neighboring organ (e.g., the neighboring organ 114B) of the subject may be captured based on insertion of the surgical image capture device in the body of the subject. In some embodiments, the internal organ of interest and the neighboring organ may be abdominal organs, for example, liver, pancreas, stomach, gall bladder and the like. The co-localization circuitry 202 may be configured to select a test video frame from the captured sequence of video frames. The co-localization circuitry 202 may be configured to generate first localization likelihood values for an internal organ of interest and second localization likelihood values for a neighboring organ having an anatomical adjacency with the internal organ of interest in the test video frame, based on training data for the internal organ of interest and the neighboring organ, and the test video frame. The co-localization circuitry 202 may be configured to determine an extent of an anatomical adjacency boundary between the internal organ of interest and the neighboring organ in the test video frame, based on a degree of correlation between the generated first localization likelihood values and the generated second localization likelihood values. The co-localization circuitry 202 may be configured to segment the test video frame into a plurality of regions. The co-localization circuitry 202 may be configured to generate a first region for the internal organ of interest by integration of a first set of regions from the plurality of regions in the segmented test video frame. The first set of regions are integrated based on a probabilistic distribution for a localization parameter for the internal organ of interest in the test video frame with respect to the anatomical adjacency boundary and a localization parameter for the neighboring organ. The co-localization circuitry 202 may be configured to localize the internal organ of interest within the body of the subject based on the generated first region, in accordance with the extent of the anatomical adjacency boundary. The generated first region may exhibit a maximum probabilistic distribution (e.g., a maximum posterior localization for the internal organ of interest, as given in equation (1)) for the localization parameter for the internal organ of interest such that the internal organ of interest and the neighboring organ are classified (or identified) in the test video frame. Also, the maximum probabilistic distribution may indicate a maximum likelihood of presence of the internal organ of interest (or a portion of the internal organ of interest) in the generated first region, in the test video frame.

In accordance with an embodiment, the co-localization circuitry 202 may be configured to select the test video frame from the captured sequence of video frames based on a presence of at least two organs in a field-of-view of the surgical image capture device. In accordance with an embodiment, the internal organ of interest may be located adjacent to the neighboring organ in the captured sequence of video frames, in accordance with the anatomical adjacency between the internal organ of interest and the neighboring organ.

In accordance with an embodiment, the co-localization circuitry 202 may be configured to extract a first set of training patches for the internal organ of interest and a second set of training patches for the neighboring organ from the training data by a random sampling technique. The co-localization circuitry may be further configured to utilize the extracted first set of training patches for generation of the first localization likelihood values and the extracted second set of training patches for generation of the second localization likelihood values. In accordance with an embodiment, the random sampling technique may be Monte Carlo sampling.

In accordance with an embodiment, the co-localization circuitry may be further configured to compare each extracted training patch of the first set of training patches with each test patch in the set of test patches of the test video frame, to generate the first localization likelihood values. The co-localization circuitry may be further configured to compare each extracted training patch of the second set of training patches with each test patch in the set of test patches of the test video frame, to generate the second localization likelihood values. In accordance with an embodiment, the first localization likelihood values of the internal organ of interest and the second localization likelihood values of the neighboring organ may be computed independent of each other.

In accordance with an embodiment, the co-localization circuitry 202 may be configured to compute the anatomical adjacency boundary between the internal organ of interest and the neighboring organ based on the generated first localization likelihood values and the generated second localization likelihood values. The extent of the anatomical adjacency boundary may be represented by an area occupied by a region in the test video frame that comprises test patches for which a correlation of the first localization likelihood values and the second localization likelihood values lies above a threshold likelihood value. In accordance with an embodiment, the co-localization circuitry may be further configured to distinguish the internal organ of interest from the neighboring organ when the extent of the computed anatomical adjacency boundary is maximum.

In accordance with an embodiment, the co-localization circuitry is further configured to output supplemental information for the generated first region for the localization of the internal organ of interest within the body of the subject. The supplemental information may comprise at least an assigned set of markers at a contour of the generated first region of the internal organ of interest. In accordance with an embodiment, the co-localization circuitry 202 may be configured to assign set of markers at the contour of the generated first region of the internal organ of interest, in the test video frame and different test video frames that are a part of the captured sequence of video frames received as a continuous video feed from the surgical image capture device. In accordance with an embodiment, the co-localization circuitry 202 may be configured to control overlay, at a display device associated with the surgical assistive device, of the supplemental information that includes the assigned set of markers, on the captured sequence of video frames displayed as a continuous feed, in real time or near-real time. In accordance with an embodiment, the co-localization circuitry 202 may be configured to generate instructions to enable navigation of a surgical instrument within the body of the subject to reach to the first region of the internal organ of interest.

In accordance with an embodiment, the co-localization circuitry 202 may be further configured to generate a second region in the test video frame for the neighboring organ by integration of a second set of regions from the plurality of regions based on the generated second localization likelihood values for the neighboring organ. In accordance with an embodiment, the co-localization circuitry 202 may be further configured to localize the neighboring organ to the generated second region in the test video frame, in accordance with the extent of the anatomical adjacency boundary. In accordance with an embodiment, the internal organ of interest may be localized post the localization of the neighboring organ. In accordance with an embodiment, the internal organ of interest and the neighboring organ may be the abdominal organs.

In accordance with an embodiment, the co-localization circuitry 202 may be further configured to compare a region in the test video frame that depicts the first localization likelihood values for the internal organ of interest with the generated first region of the test video frame. A comparison is made to identify a difference in region occupied by the internal organ of interest in the generated first region and a region in the test video frame based on the first localization likelihood values.

Various embodiments of the disclosure may provide a non-transitory computer readable medium and/or storage medium, and/or a non-transitory machine readable medium and/or storage medium with a machine code and/or instructions stored thereon and executable by a machine and/or a computer to provide assistance in a surgery. The set of instructions in the surgical assistive device 102 may cause the machine and/or computer to perform the steps that comprise reception of the plurality of training images of the internal organ of interest 112 from the medical data server 106 (FIG. 1). A sequence of video frames of one or more internal organs of subject may be captured based on insertion of the surgical image capture device 104 in the body of a subject (e.g., the human subject 112). A test video frame may be selected from the captured sequence of video frames. A first localization likelihood values may be generated for an internal organ of interest and second localization likelihood values for a neighboring organ, having an anatomical adjacency with the internal organ of interest in the test video frame, based on training data for the internal organ of interest and the neighboring organ, and the test video frame. An extent of an anatomical adjacency boundary may be determined between the internal organ of interest and the neighboring organ in the test video frame, based on a degree of correlation between the generated first localization likelihood values and the generated second localization likelihood values. The test video frame may be segmented into a plurality of regions and a first region for the internal organ of interest may be generated by integration of a first set of regions from the plurality of regions in the segmented test video frame. The first set of regions are integrated based on a probabilistic distribution for a localization parameter for the internal organ of interest in the test video frame with respect to the anatomical adjacency boundary and a localization parameter for the neighboring organ. The internal organ of interest may be localized to the generated first region in the test video frame, in accordance with the extent of the anatomical adjacency boundary. The generated first region may exhibits a maximum probabilistic distribution for the localization parameter for the internal organ of interest such that the internal organ of interest and the neighboring organ are precisely classified in the test video frame.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features that enable the implementation of the methods described herein, and which when loaded in a computer system is able to carry out these methods. Computer program, in the present context, means any expression, in any language, code or notation, of a set of instructions intended to cause a system that has an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without departure from the scope of the present disclosure. In addition, many modifications may be made to adapt a particular situation or material to the teachings of the present disclosure without departure from its scope. Therefore, it is intended that the present disclosure not be limited to the particular embodiment disclosed, but that the present disclosure will include all embodiments that falls within the scope of the appended claims.

What is claimed is:

1. A surgical assistive device, comprising:
a surgical image capture device configured to capture a sequence of video frames based on insertion of the surgical image capture device in a body of a subject; and
co-localization circuitry configured to:
generate first localization likelihood values for an internal organ of interest and second localization likelihood values for a neighboring organ having an anatomical adjacency with the internal organ of interest in a test video frame of the captured sequence of video frames;
determine an extent of an anatomical adjacency boundary between the internal organ of interest and the neighboring organ in the test video frame, based on the generated first localization likelihood values and the generated second localization likelihood values;
segment the test video frame into a plurality of regions;
generate a first region for the internal organ of interest based on integration of a first set of regions from the plurality of regions in the segmented test video frame, wherein the first set of regions are integrated based on a conditional probabilistic distribution for a localization parameter for the internal organ of interest in the test video frame with respect to the anatomical adjacency boundary and a localization parameter for the neighboring organ; and
localize the internal organ of interest within the body of the subject based on the generated first region in accordance with the extent of the anatomical adjacency boundary.

2. The surgical assistive device according to claim 1, wherein the co-localization circuitry is further configured to select the test video frame from the captured sequence of video frames based on a presence of at least two organs in a field-of-view of the surgical image capture device.

3. The surgical assistive device according to claim 1, wherein the internal organ of interest is located adjacent to the neighboring organ in the captured sequence of video frames, in accordance with the anatomical adjacency between the internal organ of interest and the neighboring organ.

4. The surgical assistive device according to claim 1, wherein the first localization likelihood values and the second localization likelihood values are generated based on the test video frame and training data for the internal organ of interest and the neighboring organ, wherein the training data is received from a medical data server.

5. The surgical assistive device according to claim 1, wherein the co-localization circuitry is further configured to extract a first set of training patches for the internal organ of interest and a second set of training patches for the neighboring organ from training data by a random sampling technique, wherein the co-localization circuitry is further configured to utilize the extracted first set of training patches for generation of the first localization likelihood values and the extracted second set of training patches for generation of the second localization likelihood values.

6. The surgical assistive device according to claim 5, wherein the random sampling technique is Monte Carlo sampling.

7. The surgical assistive device according to claim 5, wherein the co-localization circuitry is further configured to:
compare each extracted training patch of the first set of training patches with each test patch in a set of test patches of the test video frame, to generate the first localization likelihood values; and
compare each extracted training patch of the second set of training patches with each test patch in the set of test patches of the test video frame to generate the second localization likelihood values.

8. The surgical assistive device according to claim 1, wherein the first localization likelihood values of the internal organ of interest and the second localization likelihood values of the neighboring organ are computed independent of each other.

9. The surgical assistive device according to claim 1, wherein the co-localization circuitry is further configured to compute the anatomical adjacency boundary between the internal organ of interest and the neighboring organ based on the generated first localization likelihood values and the generated second localization likelihood values, wherein the extent of the anatomical adjacency boundary is represented by an area occupied by a region in the test video frame that comprises test patches for which a correlation of the first localization likelihood values and the second localization likelihood values lies above a threshold likelihood value.

10. The surgical assistive device according to claim 9, wherein the co-localization circuitry is further configured to utilize the computed anatomical adjacency boundary to distinguish the internal organ of interest from the neighboring organ when the extent of the computed anatomical adjacency boundary is maximum.

11. The surgical assistive device according to claim 1, wherein the generated first region exhibits a maximum probabilistic distribution for the localization parameter for the internal organ of interest such that the internal organ of interest and the neighboring organ are classified in the test video frame.

12. The surgical assistive device according to claim 1, wherein the co-localization circuitry is further configured to output supplemental information for the generated first region for the localization of the internal organ of interest within the body, wherein the supplemental information comprises at least an assigned set of markers at a contour of the generated first region of the internal organ of interest.

13. The surgical assistive device according to claim 1, wherein the co-localization circuitry is further configured to assign a set of markers at a contour of the generated first region of the internal organ of interest, in the test video frame and different test video frames that are a part of the captured sequence of video frames received as a continuous video feed from the surgical image capture device.

14. The surgical assistive device according to claim 13, wherein the co-localization circuitry is further configured to control overlay, at a display device associated with the surgical assistive device, of supplemental information that includes the assigned set of markers, on the captured sequence of video frames displayed as a continuous feed, in real time or near-real time.

15. The surgical assistive device according to claim 1, wherein the co-localization circuitry is further configured to generate instructions to enable navigation of a surgical instrument within the body of the subject to reach to the first region of the internal organ of interest.

16. The surgical assistive device according to claim 1, wherein the co-localization circuitry is further configured to generate a second region in the test video frame for the neighboring organ by integration of a second set of regions from the plurality of regions based on the generated second localization likelihood values for the neighboring organ.

17. The surgical assistive device according to claim 16, wherein the co-localization circuitry is further configured to localize the neighboring organ based on the generated second region in the test video frame, in accordance with the extent of the anatomical adjacency boundary.

18. The surgical assistive device according to claim 1, wherein the internal organ of interest is localized post the localization of the neighboring organ.

19. The surgical assistive device according to claim 1, wherein the internal organ of interest and the neighboring organ are abdominal organs.

20. The surgical assistive device according to claim 1, wherein the co-localization circuitry is further configured to compare a region in the test video frame that depicts the first localization likelihood values for the internal organ of interest with the generated first region of the test video frame, wherein a comparison is made to identify a difference in region occupied by the internal organ of interest in the generated first region and a region in the test video frame based on the first localization likelihood values.

21. A method, comprising:
  in a surgical assistive device that comprises a surgical image capture device and co-localization circuitry:
  capturing, by the surgical image capture device, capture a sequence of video frames, based on insertion of the surgical image capture device in a body of a subject;
  generating, by the co-localization circuitry, first localization likelihood values for an internal organ of interest and second localization likelihood values for a neighboring organ having an anatomical adjacency with the internal organ of interest in a test video frame selected from the captured sequence of video frames;
  determining, by the co-localization circuitry, a extent of an anatomical adjacency boundary between the internal organ of interest and the neighboring organ in the test video frame, based on the generated first localization likelihood values and the generated second localization likelihood values;
  segmenting, by the co-localization circuitry, the test video frame into a plurality of regions;
  generating, by the co-localization circuitry, a first region for the internal organ of interest by integration of a first set of regions from the plurality of regions in the segmented test video frame, based on a conditional probabilistic distribution for a localization parameter for the internal organ of interest in the test video frame with respect to the anatomical adjacency boundary and a localization parameter for the neighboring organ; and
  localizing, by the co-localization circuitry, the internal organ of interest within the body of the subject based on the generated first region in the test video frame, in accordance with extent of the anatomical adjacency boundary.

\* \* \* \* \*